(12) United States Patent
Mostafa et al.

(10) Patent No.: US 11,960,524 B2
(45) Date of Patent: Apr. 16, 2024

(54) METHODS, SYSTEMS, AND COMPUTER READABLE MEDIA FOR DYNAMIC CLUSTER-BASED SEARCH AND RETRIEVAL

(71) Applicant: The University of North Carolina at Chapel Hill, Chapel Hill, NC (US)

(72) Inventors: Javed Mostafa, Cary, NC (US); Michael Segundo Ortiz, Chapel Hill, NC (US); Kazuhiro Seki, Kobe (JP); Mengqian Wang, Chapel Hill, NC (US); Heejun Kim, Bryn Mawr, PA (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 17/902,583

(22) Filed: Sep. 2, 2022

(65) Prior Publication Data
US 2023/0004592 A1    Jan. 5, 2023

Related U.S. Application Data

(63) Continuation of application No. PCT/US2021/020524, filed on Mar. 2, 2021.
(Continued)

(51) Int. Cl.
*G06F 16/00* (2019.01)
*G06F 16/33* (2019.01)
(Continued)

(52) U.S. Cl.
CPC ........ *G06F 16/358* (2019.01); *G06F 16/3334* (2019.01); *G06F 40/30* (2020.01); *G16H 70/60* (2018.01)

(58) Field of Classification Search
CPC ....... G06F 16/358; G06F 40/30; G16H 70/60; G05F 16/3334
(Continued)

(56) References Cited

U.S. PATENT DOCUMENTS

| 6,574,378 B1 * | 6/2003 | Lim ................... G06F 16/5854 707/E17.024 |
| 7,778,988 B2 * | 8/2010 | Tateno ................ G06F 16/353 707/726 |

(Continued)

FOREIGN PATENT DOCUMENTS

| JP | 2004094813 A | * | 3/2004 |
| KR | 20120061239 A | | 6/2012 |
| KR | 20190097669 A | | 8/2019 |

OTHER PUBLICATIONS

Ben-David, "A framework for statistical clustering with constant time approximation algorithms for K-median and K-means clustering", Springer Science + Business Media, LLC 2007, Nov. 30, 2006, pp. 243-257.*

(Continued)

*Primary Examiner* — Monica M Pyo
(74) *Attorney, Agent, or Firm* — Jenkins, Taylor & Hunt, P.A.

(57) ABSTRACT

The subject matter described herein relates to methods, systems, and computer readable media for dynamic cluster-based search and retrieval. An example method for dynamic cluster-based search and retrieval occurs at a server. The method includes: retrieving document data for a plurality of documents related to user input; performing keyword discovery on the document data for determining term related frequency metrics and document related frequency metrics; representing the plurality of documents as a term-document matrix based on the term related frequency metrics and the document related frequency metrics; reducing, using latent (Continued)

semantic analysis, the dimensionality of the matrix; clustering, using a k-means clustering algorithm and the dimensionally reduced matrix, the plurality of documents into clusters; and sending presentation information to a client device for displaying visual representations of the clusters, wherein each visual representation is associated with one or more of the plurality of documents.

16 Claims, 11 Drawing Sheets

Related U.S. Application Data

(60) Provisional application No. 62/984,782, filed on Mar. 3, 2020.

(51) Int. Cl.
    *G06F 16/35*     (2019.01)
    *G06F 40/30*     (2020.01)
    *G16H 70/60*     (2018.01)

(58) Field of Classification Search
    USPC .......................................................... 707/737
    See application file for complete search history.

(56) References Cited

U.S. PATENT DOCUMENTS

| | | | | |
|---|---|---|---|---|
| 10,216,724 | B2 * | 2/2019 | Sinha | G06F 40/30 |
| 2010/0223276 | A1 * | 9/2010 | Al-Shameri | G06F 16/3347 707/769 |
| 2012/0209847 | A1 * | 8/2012 | Rangan | G06F 16/3347 707/769 |
| 2012/0296891 | A1 * | 11/2012 | Rangan | G06F 16/3347 707/E17.014 |
| 2012/0330955 | A1 | 12/2012 | Miura | |
| 2014/0282244 | A1 | 9/2014 | Speer et al. | |
| 2015/0310010 | A1 * | 10/2015 | Brenner | G06F 16/5866 707/730 |
| 2018/0127744 | A1 * | 5/2018 | Hu | G16B 45/00 |

OTHER PUBLICATIONS

Bejarano et al., "Sampling Within k-Means Algorithm to Cluster Large Datasets", Technical Report HPCF-2011-12, 2010, 11 pages.*
Ackermann et al., "StreamKM++: A Clustering Algorithm for Data Streams", Acm J. Exp. Algor. 17, 2, Article 2.4, May 2012, 30 pages.*
Notification of Transmittal of the International Search Report and the Written Opinion of the International Searching Authority, or the Declaration for International Application No. PCT/US2021/020524 (dated Jul. 6, 2021).
Das et al., "Reducing dimensionality of text documents using latent semantic analysis," International Journal of Computer Applications, pp. 1-5 (Mar. 2015).
Moon et al., "Improving CRISPR Genome Editing by Guide RNAs," Trends in Biotechnology, vol. 37, No. 8, pp. 870-881 (Aug. 2019).
Teng et al., "Artificial sgRNAs engineered for genome editing with new Cas12b orthologs," Cell Discovery, vol. 5 No. 23, pp. 1-4 (2019).
Farooq et al., "CRISPR/Cas9; A robust technology for producing genetically engineered plants," Cellular and Molecular Biology, pp. 1-9 (2018).
Ghosh et al., "Searching as Learning: Exploring Search Behavior and Learning Outcomes in Learning-Related Tasks," CHIIR'18, pp. 22-31 (2018).
Ortiz et al., "Toward Exploratory Search in Biomedicine: Evaluating Document Clusters by MeSH as a Semantic Anchor," CoRR arXiv:1812.02129, https://arxiv.org/abs/1812.02129, pp. 1-5 (2018).
Ruotsalo et al., Interactive Intent Modeling for Exploratory Search, ACM Transactions on Information Systems, vol. 36, No. 4, Article 44, pp. 1-46 (Oct. 2018).
Shi et al., "Workshop Proposal on Knowledge Discovery from Digital Libraries," JCDL'18, pp. 1-2 (Jun. 2018).
Batzir et al., "Therapeutic Genome Editing and its Potential Enhancement through CRISPR Guide RNA and Cas9 Modification," Ped. Endocrinol. Rev., vol. 14, No. 4, pp. 353-363 (2017).
Sciascio et al., "Supporting Exploratory Search with a Visual User-Driven Approach," ACM Trans. Interact. Intell. Syst., vol. 7, No. 4, Article 18, pp. 1-35 (Dec. 2017).
Hansen et al., "Recent advances on searching as learning: An introduction to the special issue," Journal of Information Science, vol. 42, No. 1, pp. 3-6 (2016).
Kelley et al., "Versatility of chemically synthesized guide RNAs for CRISPR-Cas9 genome editing," Journal of Biotechnology, vol. 233, pp. 1-10 (2016).
Romano et al., "Adjusting for Chance Clustering Comparison Measures," Journal of Machine Learning Research, vol. 17 pp. 1-32 (2016).
Ruotsalo et al., "Interactive Intent Modeling: Information Discovery Beyond Search," Communications of the ACM vol. 58, No. 1, pp. 86-92 (Jan. 2015).
Gong et al., "Interactive Search Result Clustering: A Study of User Behavior and Retrieval Effectiveness," JCDL'13, pp. 167-170 (2013).
Sculley, "Web-Scale K-Means Clustering," WWW 2010, pp. 1177-1178 (2010).
Kules et al., "What Do Exploratory Searchers Look at in a Faceted Search Interface?" JCDI'09, pp. 313-322 (2009).
White et al., "Exploratory Search," Synthesis lectures on information concepts, retrieval, and services, vol. 1, No. 1, pp. 1-102 (2009).
Maaten et al., "Visualizing Data using t-SNE," Journal of Machine Learning Research, vol. 9, pp. 2579-2605 (2008).
Arthur et al., "k-means++: The Advantages of Careful Seeding," In Proceedings of the eighteenth annual ACM-SIAM symposium on Discrete algorithms. Society for Industrial and Applied Mathematics, pp. 1-9 (2007).
Marchionini, "Exploratory Search: From Finding to Understanding," Communications of the ACM, vol. 49, No. 4, pp. 1-7 (Apr. 2006).
White et al., "Supporting Exploratory Search," Communications of the ACM, vol. 49, No. 4, pp. 1-4 (Apr. 2006).
Wilson et al., "mSpace: Improving information access to multimedia domains with Multimodal exploratory search," Communications of the ACM, vol. 49, No. 4, pp. 1-4 (2006).
Landauer et al., "An Introduction to Latent Semantic Analysis," Disclosure Processes, vol. 25, No. 2 & 3, pp. 259-284 (1998).
Mostafa et al., "Filtering Medical Documents Using Automated and Human Classification Methods," Journal of the American Society for Information Science, pp. 1304-1318 (1998).
Hearst et al., "Reexamining the Cluster Hypothesis: Scatter/Gather on Retrieval Results," In the Proceedings of ACM SIGIR '96, pp. 1-9 (Aug. 1996).
Shneiderman, "The Eyes Have It: A Task by Data Type Taxonomy for Information Visualizations," IEEE, pp. 336-343 (1996).
Cutting et al., "Constant Interaction-Time Scatter/Gather Browsing of Very Large Document Collections," ACM-SIGIR'93-6, pp. 126-134 (1993).
Cutting et al., "Scatter/Gather: A Cluster-based Approach to Browsing Large Document Collections," 15th Ann Int'l SIGIR '92, pp. 148-159 (1992).
Rijsbergen, "Information Retrieval," Butterworth-Heinemann, Newton, MA, USA, pp. 1-153 (1979).
Jones, "A statistical interpretation of term specificity and its application in retrieval," Journal of Documentation, vol. 28, No. 1 pp. 1-9 (1972).

\* cited by examiner

FIG. 8

METHODS, SYSTEMS, AND COMPUTER READABLE MEDIA FOR DYNAMIC CLUSTER-BASED SEARCH AND RETRIEVAL

PRIORITY CLAIM

This application is a continuation of PCT Application No. PCT/US2021/020524 filed Mar. 2, 2021, which claims the priority benefit of U.S. Provisional Patent Application Ser. No. 62/984,782, filed Mar. 3, 2020, the disclosure of each of which is incorporated by reference herein in its entirety.

GOVERNMENT INTEREST

This invention was made with government support under Grant No. LM012500 awarded by the National Institutes of Health. The government has certain rights in the invention.

TECHNICAL FIELD

The subject matter described herein relates to computer-based data search and retrieval. More particularly, the subject matter described herein relates to methods, systems, and computer readable media for dynamic cluster-based search and retrieval.

BACKGROUND

Due to increased specialization and experimentation in various fields, the volume of data (e.g., research data, biomedical literature, etc.) is rapidly increasing. As such, the current modalities for search and retrieval can no longer support effective and efficient knowledge discovery. Some information retrieval systems, such as PubMed, make assumptions as to users' prior knowledge and expect them to formulate a proper query term for the information they are looking for. While these systems may provide user feedback mechanisms to help users reformulate their queries, such mechanisms still assume that users know how the search results can be effectively narrowed down by way of additional keywords and/or filters.

Accordingly, there exists a need for methods, systems, and computer readable media for dynamic cluster-based search and retrieval.

SUMMARY

The subject matter described herein relates to methods, systems, and computer readable media for dynamic cluster-based search and retrieval. An example method for dynamic cluster-based search and retrieval occurs at a server. The method includes: retrieving document data for a plurality of documents related to user input; performing keyword discovery on the document data for determining term related frequency metrics and document related frequency metrics; representing the plurality of documents as a term-document matrix based on the term related frequency metrics and the document related frequency metrics; reducing, using latent semantic analysis, the dimensionality of the matrix; clustering, using a k-means clustering algorithm and the dimensionally reduced matrix, the plurality of documents into clusters; and sending presentation information to a client device for displaying visual representations of the clusters, wherein each visual representation is associated with one or more of the plurality of documents.

An example system for dynamic cluster-based search and retrieval includes at least one computing platform including at least one processor; and a search and retrieval application executable by the at least one processor for: retrieving document data for a plurality of documents related to user input; performing keyword discovery on the document data for determining term related frequency metrics and document related frequency metrics; representing the plurality of documents as a term-document matrix based on the term related frequency metrics and the document related frequency metrics; reducing, using latent semantic analysis, the dimensionality of the matrix; clustering, using a k-means clustering algorithm and the dimensionally reduced matrix, the plurality of documents into clusters; and sending presentation information to a client device for displaying visual representations of the clusters, wherein each visual representation is associated with one or more of the plurality of documents.

Various technical effects are achieved by implementing one or more aspects described herein. One technical effect involves automatically identifying related documents or terms therein and presenting those relationships in a concise and effective way. For example, an example system for cluster-based search and retrieval can improve search and retrieval of various documents (e.g., scientific, highly specialized, and/or information-dense research papers) by grouping the documents into one or more clusters using a k-means clustering algorithm and a term-document matrix. In this example, the clusters can provide a concise and effective way to present the related documents or terms therein to a user and/or another entity (e.g., a document management system).

Another technical effect involves performing dynamic clustering of documents or terms therein using a scatter and gather (scatter/gather) model associated with user input. For example, an example system for cluster-based search and retrieval may provide a graphical user interface (GUI) or other user interface for allowing a user to select a subset of displayed clusters, where the subset of clusters may represent a subset of all available documents (e.g., a gather operation) and for allowing the user to then trigger the system (e.g., via the GUI or interface) to perform a (re-)grouping of the subset of documents into one or more clusters using a k-means clustering algorithm and a new term-document matrix associated with the selected subset of documents (e.g., a scatter operation). In this example, the resulting clusters can provide a concise and effective way to present related topics or terms involving the subset of documents to the user and/or other entity (e.g., a document management system). In another example, an example system for cluster-based search and retrieval may provide a GUI or other user interface for allowing a user to select a single cluster representing a set of related documents (e.g., a gather operation) and for allowing the user to then trigger the system (e.g., via the GUI or interface) to perform a (re-)grouping of the documents in the cluster into one or more clusters using a k-means clustering algorithm and a new term-document matrix associated with the selected set of documents (e.g., a scatter operation). In this example, the resulting clusters can provide a concise and effective way to present additional or different related topics or terms (e.g., subtopics) involving the documents to the user and/or other entity (e.g., a document management system). Hence, by using dynamic clustering and gather and scatter operations, the system can allow a user to direct information exploration and provide relevant information with varying levels of details or scope.

Another technical effect involves effectively presenting a set of related documents or terms therein using a visual element containing one or more relevant keywords or terms, where the relevant keywords or terms are determined using an objective algorithm or technique. For example, an example system for cluster-based search and retrieval may provide a GUI or other user interface for displaying an initial set of clusters, where each cluster represents a set of related documents and is labeled with one or more relevant keywords. In this example, the system may determine keywords for a respective cluster by identifying a centroid of the cluster (e.g., as based on the coordinates of the cluster in a two-dimensional space (e.g., of a GUI or panel therein); transforming (e.g., using stored mappings between centroids of clusters and related term vectors) the centroid to a term vector containing term frequency information; and determining the keywords based on terms with the highest frequencies as indicated by the term vector.

Another technical effect involves overcoming time complexity issues and/or processing speed requirements associated with generating and presenting dynamic clustering search results in constant time or near constant time. While existing clustering algorithms running in constant time typically rely on a pre-computed static hierarchy of categories (which is not suited for iterative, dynamic cluster-based searching), an example system for cluster-based search and retrieval in accordance with various aspects described herein can overcome such issues by using a sampling-based clustering approach. For example, instead of limiting search results to a predefined number of clusters, an example system for cluster-based search and retrieval may performing dynamic clustering using an N number of latest documents (e.g., most recent articles based on publication or submission date) for a given query. In this example, even though the time complexity of a clustering algorithm itself (k-means) may not be constant, the clustering process can still complete approximately in constant time for a fixed N and may also yield a variable number of clusters. In some examples, additional factors or parameters can be changed or adjusted depending on variety of factors for improving speed, scope, or clustering efficiency, including e.g., the size or portion of each document to be analyzed (e.g., the system may be configured to analyze a title, an abstract, or a summary section in lieu of the full text) and/or the number of documents analyzed for each search or clustering operation (e.g., the system may be configured to change the number of documents for initial clustering from 2000 to 20000 or from 2000 to 1000).

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

FIG. 8 is a diagram illustrating search results for a query "genomic editing" using the PubMed Central website;

DETAILED DESCRIPTION

Figure 1:
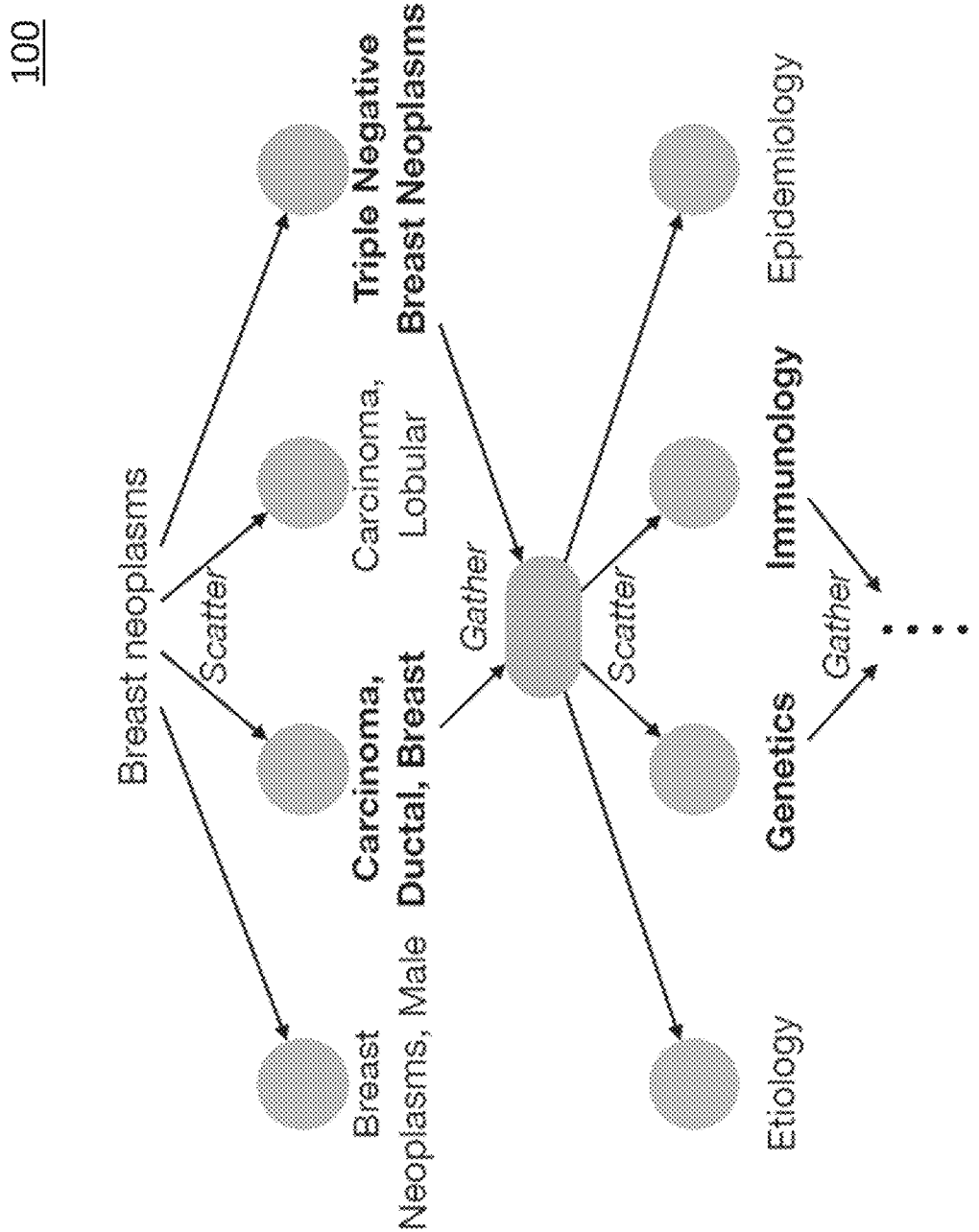
FIG. 1 is a diagram illustrating an example scatter/gather browsing paradigm.

The subject matter described herein relates to methods, systems, and computer readable media for dynamic cluster-based search and retrieval. Reference will now be made in detail to various embodiments of the subject matter described herein, examples of which are illustrated in the accompanying drawings. Wherever possible, the same reference numbers will be used throughout the drawings to refer to the same or like parts.

In accordance with some aspects of the subject matter described herein, techniques, methods, or mechanisms are disclosed for dynamic cluster-based search and retrieval. For example, an example search and retrieval system may utilize dynamic clustering and scatter/gather operations to facilitate information exploration by presenting search results as visual representations of clusters, e.g., clusters may be depicted as circles containing keywords associated with corresponding clusters. In this example, the search and retrieval system may be configured for retrieving document data for a plurality of documents related to user input; performing keyword discovery on the document data for determining term related frequency metrics and document related frequency metrics; representing the plurality of documents as a term-document matrix based on the term related frequency metrics and the document related frequency metrics; reducing, using latent semantic analysis, the dimensionality of the matrix; clustering, using a k-means clustering algorithm and the dimensionally reduced matrix, the plurality of documents into clusters; and sending presentation information to a client device for displaying visual representations of the clusters, wherein each visual representation is associated with one or more of the plurality of documents.

Advantageously, in accordance with some aspects of the subject matter described herein, by using dynamic clustering and a visual or graphical user interface, related search results can be presented to a user in a visually informative way and can aid the user in their information exploration, especially for dense information spaces. Further, by using a scatter/gather model, a user can identify related topics and search terms (gather) and then have those identified or gathered topics and terms re-evaluated for additional and/or different relationships (scatter) without having prior understanding of terminology or information space structure.

1. Introduction

Automated clustering of scientific publications and spatial encoding of information visualization techniques is of emerging importance for digital libraries [24]. This is especially true for biomedical libraries. The current ranking-based retrieval model assumes that users have a clear understanding of the information need and thus could formulate a proper query that facilitates a ranked list of various information types that are in descending order of relevancy. However, prior understanding of terminology or information space structure may not exist [29, 31]. Moreover, even with a properly formulated query in biomedicine, a flat list of thousands of results does not enable discovery of latent information, logical connections among concepts, or transitive properties within a particular information space; processes of which can be automated and packaged as a real-time generative model to aid researchers in their information exploration and hypothesis generation.

The current mode of access, generally speaking, is a look-up procedure, similar to searching an index in a large textbook. To ultimately improve access, it seems intuitive to provide a table of contents metaphor for users to explore what topical content is in a collection and iteratively reach a more specific information target; a process called exploratory search [12, 30]. For example, this paradigm is also utilized by the 2012 ACM Computing Classification System (CCS) whereby you can generate codes to classify conference documents and also iteratively reach highly relevant literature based on topical content. Such an interactive ontology would be tremendously useful for Medical Subject Headings (MeSH) given that PubMed is arguably the largest biomedical literature base in the world, for example. These classification models serve as very powerful filtering tools to narrow the focus of a search. However, there is also the need to build robust tools on top of these paradigms that model spatial semantics and latent information structure in order to enable discovery and generate hypotheses.

In this work, we discuss an example system for exploring topical content in the biomedical literature. The organization of this work is as follows. In the related work section, we discuss the benefits and limitations of other exploratory information retrieval systems in biomedicine and propose a revival of the scatter/gather dynamic clustering paradigm. In the system architecture and description sections, we discuss the data flow from server to client, data processing, and visualization. Lastly, we provide a use-case for retrieving information on genomic editing and briefly contrast this with a conventional search in PubMed.

2. Related Work

In this section, we will briefly introduce previous work on exploratory search systems and the various modalities they employ. On the user end, classic retrieval optimization involves incremental feedback to search systems in terms of revised queries. However, practice shows that the added step of revising queries is non-desirable [13]. Moreover, some evidence suggests that users spend the least amount of time on queries and focus more on results and facets or filters of retrieved information [10]. Other research indicates that complex search tasks may result in longer queries which implies that more thought or prior knowledge must go into such a query [5]. These findings indicate that exploratory information systems can be a more intuitive model when search intent is unclear. User feedback is essential, however, revising queries appears to be an inferior method.

Routsalo et al. [20, 21] developed a system called SciNet, specifically targeting interactive user intent modeling. User intent is often vague, and proper query terms may not be known or provided by a user. SciNet attempts to solve this problem by an interactive visual interface. The system starts with a user query and returns a wide spectrum of keywords to suggest potential intents on a radar chart-like screen in addition to a standard ranked list of documents. On the radar screen, users can give their feedback by moving any keywords they find relevant to the center of the radar, and vice versa. Given the feedback, the system updates the estimate of the user intent and dynamically updates the results.

Sciascio et al. [22] developed another system called uRank. The system provides a keyword list summarizing a document collection and a document list showing a ranked list of documents with stacked bars of relevance scores for each keyword. The users choose keywords from the keyword list and, for each keyword, its weight can be adjusted by a slider. The rankings of the documents are dynamically changed reflecting the chosen keywords and their weights. The stacked bars of relevance scores help the users to see how much each document is relevant with respect to individual keywords.

Another approach is scatter/gather [3, 4, 8]. Scatter/gather is a browsing-based information exploratory model and presents topically coherent groups (clusters) of documents with descriptive textual summaries as opposed to a ranked list of documents. In other words, documents are "scattered" into topical clusters for browsing. A user can browse the generated clusters and "gather" the ones that are interesting or relevant. Based on the selection, the documents in the selected clusters are re-clustered and presented to the users again. This process is repeated until a user feels they have identified their information target.

FIG. 1 is a diagram 100 illustrating an example scatter/gather browsing paradigm. This particular example starts with a query "Breast Neoplasms" to form a document collection and scatters four topical clusters (i.e., Breast Neoplasms Male, Carcinoma Ductal Breast, etc.). The user then gathers two clusters of interest: Carcinoma Ductal, Breast and Triple Negative Breast Neoplasms, then four new and more specific clusters (i.e., Etiology, Epidemiology, etc.) are identified within the selected clusters and gathered/scattered again on Immunology and Genetics, indicating the users' interest in immunologic and genetic information in relation to the specified forms of breast neoplasms selected in the first scatter phase. This scatter/gather browsing is particularly helpful in cases where a user is unsure about formulating a specific search query because it allows him/her to explore the general content of a collection and iteratively refine their information need based on the relationships among concepts.

Scatter/gather is built on the cluster hypothesis [17], which states that "closely associated documents tend to be relevant to the same requests". Because multiple documents are clustered into topically related groups, the scatter/gather browsing model may reduce user burden by providing a dynamic table of contents metaphor as opposed to querying a collection with vague intent and then scrolling through a potentially large set of individual documents which we analogize to searching a vast textbook-like index.

The effectiveness of scatter/gather has been empirically investigated by several studies. Hearst et al. [8] reported that relevant documents for a given query tended to be clustered together and that the users were able to choose the right cluster with the largest number of relevant documents in more than 80% of cases. Gong et al. [6] also reported that this model was found to be particularly helpful for search tasks unfamiliar to users. Ortiz et al. [16] examined a more fundamental question of the effectiveness of cluster-based browsing models and systematically studied various parameters affecting cluster quality.

Despite its potential benefits, a cluster-based browsing search interface has not been extensively studied for biomedical literature primarily due to two challenges. First, clustering should be fast for an arbitrarily large number of documents. The Buckshot clustering algorithm [4] proposed with scatter/gather runs in time O(kn) where k is the number of clusters, but linear time is still not fast enough to execute clustering on the fly for a large document collection. A constant time algorithm was also proposed [3], which builds a static hierarchy of clusters in advance in an offline process. However, appropriate grouping of documents can change both for an initial query and for chosen clusters [8], and thus a static cluster structure is often sub-optimal. The second challenge is to develop an intuitive and effective user interface. In the past, much work adopting scatter/gather simply used text-based interface, and it is unclear how document clusters and scatter/gather mechanisms are best visualized.

3. Dynamic Cluster-Based Browsing

This section describes the design and implementation details of our dynamic cluster-based browsing system, $DCB^2$. We adopt the scatter/gather paradigm for its potential and tackle the open issues concerning real-time clustering, dynamicity, and effective interface design.

3.1 Overview

Figure 2:
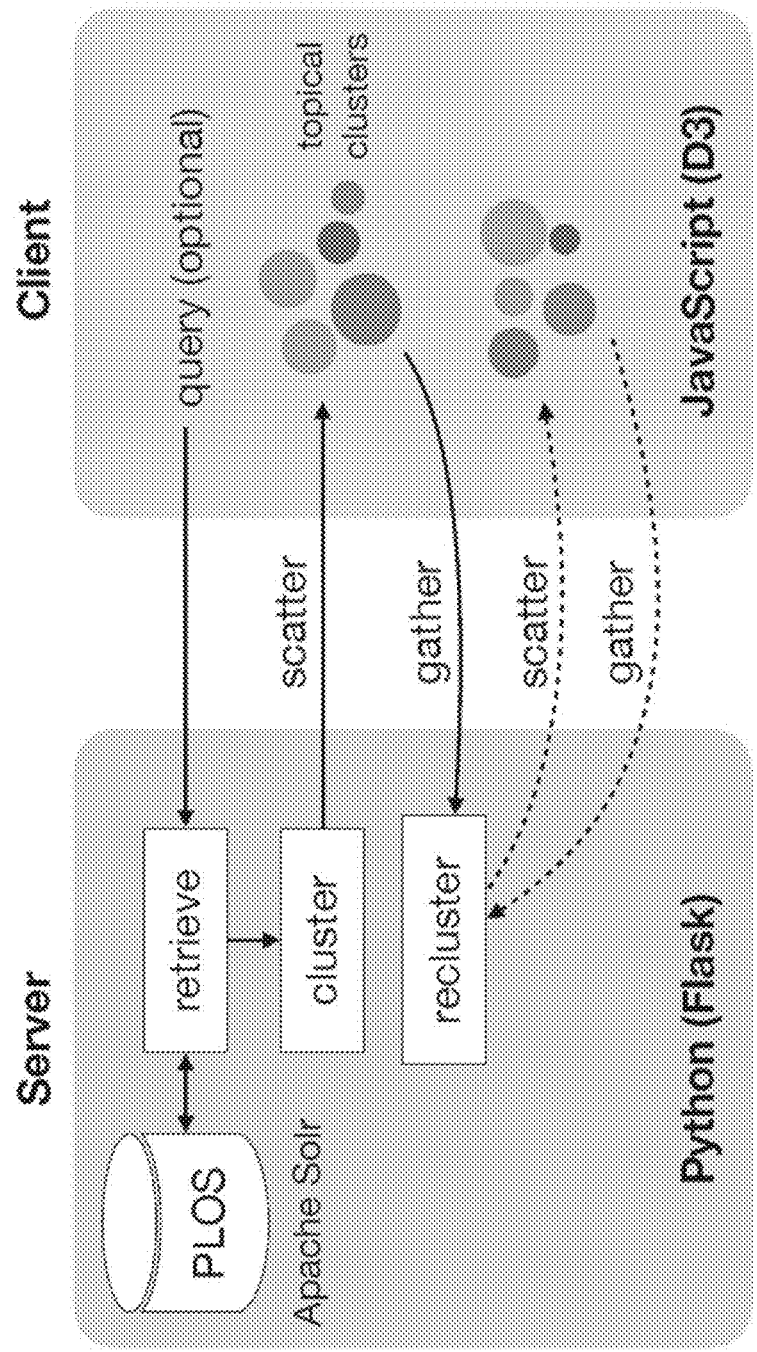
FIG. 2 is a diagram illustrating an example system architecture for dynamic cluster-based search and retrieval.

FIG. 2 is a diagram 200 illustrating an example system architecture for dynamic cluster-based search and retrieval (e.g., $DCB^2$) and related data flow, where the dotted lines indicate iterative processes by a user. The server-side system runs on Amazon Web Services Elastic Cloud Compute (AWS EC2) and is implemented by the Flask web framework. The document collection was downloaded from the Public Library of Science (PLOS), indexed by Apache Solr, and locally resides in the server for efficiency. The client-side is built on a JavaScript visualization library D3.js. For interactive and iterative browsing, the client uses Ajax to asynchronously communicate with the server which eliminates the need to reload the web page as content is dynamically explored. The following sections describe various components of the system in more detail.

3.2 Initial Data Retrieval and Clustering

Figure 3:
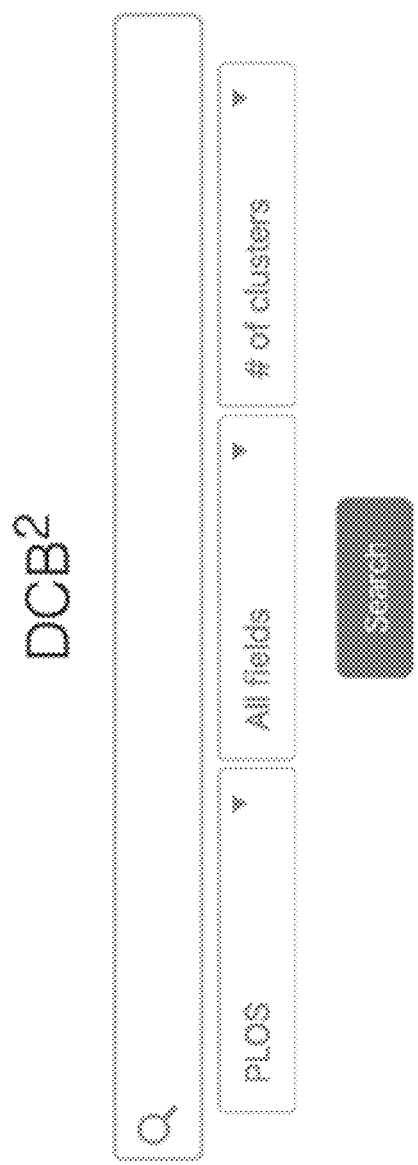
FIG. 3 is a diagram illustrating an example start page for search.

FIG. 3 is a diagram illustrating an example start page 300 for search. As depicted in FIG. 3, $DCB^2$ starts with a text box for a user query as with other keyword-based search systems, although our system can initiate information retrieval with or without a query. When a query is given, it retrieves N latest articles satisfying the query. When no query is given, it simply retrieves N latest articles in the collection without considering any particular topic. We fix N to a constant value so that clustering is completed in constant time regardless of a query, facilitating real-time processing. The rationale behind this design is random sampling in order to deal with the potentially large number of documents. This is similar to the idea of a mini-batch k-means algorithm [23]. The mini-batch k-means algorithm may first perform k-means clustering on a random subset of data to compute cluster centroids and then determines the membership of all the data points. This mini-batch k-means is reported to converge to near-optima several orders of magnitude faster than standard k-means. Instead of complete randomness, however, our prototype system favors recency (e.g., based on publication dates) as we are generally interested in more recent information in the biomedical domain. Although limiting the number of documents by N will certainly influence the resulting cluster structure, we assume the effect is limited for a large N. We will investigate the validity of this assumption in Section 4.

As for query language, $DCB^2$ can understand a wide range of query syntax accepted by Solr, such as Boolean queries, range queries, phrases, and wild cards. However, we expect more general queries since our system focuses on exploratory search where a user's search intent is not yet clear. Currently, the system retrieves titles, abstracts, and body texts and concatenates them, but other data including journal names, authors, and affiliations are also indexed and readily available for future use. Note that the search field (default is "all fields") and the number of clusters (default is "10") can be specified by the search page for convenience.

After retrieving the article information, the prototype system executes the following processes in this order, which was reported to be beneficial for constructing high quality clusters [16].

Keyword discovery: The system first identifies prominent terms to represent the retrieved document set. For this purpose, we adopt a statistical approach called Vocabulary Cluster Generating System (VCGS) [15]. VCGS discovers keywords based on term and document frequencies. Using only the discovered keywords, the document set is represented as a term-document matrix M with tf-idf term weighting [26]. This process greatly reduces the data size.

Latent semantic analysis (LSA) [11]: To further reduce the dimensionality of the term-document matrix M and to discover latent associations among keywords, LSA is applied to M. LSA is a matrix decomposition technique that extracts and represents the contextual usage of terms in a collection of documents. The transformation of a full-featured matrix to a dimensionally reduced matrix helps reveal implicit semantic associations between documents. The dimensionally reduced matrix can be obtained by first decomposing M into $U\Sigma V^T$, where U and V are orthogonal matrices and $\Sigma$ is a diagonal matrix with the eigenvalues of the eigenvectors in descending order. The first n rows of matrix V (corresponding to the n largest singular values in $\Sigma$) is the n dimensionally reduced matrix. Currently, we empirically use 50 as the number of components (dimensions).

Clustering: The document set is then topically clustered for presentation. We use the k-means++ algorithm [1], where k is set to 10 by considering the trade-off between readability and informativeness. Alternatively, users can choose the value of k from 2 to 10 via a GUI, e.g., start page 300.

After these processes, the system generates a set of keywords to describe each cluster for the next visualization stage. More precisely, the centroid of each cluster in the LSA-reduced space is transformed back to the original term-document space and is represented as a term vector. From the vector, keywords with n highest tf-idf values are selected as the description of the cluster. In addition, the centroids in the LSA-reduced space are transformed to coordinate space by t-Distributed Stochastic Neighbor Embedding (t-SNE) [28] and plotted in 2D. Only the descriptions (keyword set) and 2D coordinates for the clusters are sent to the client for efficiency, and other information may be retained as session data on the server.

3.3 Visualization

We designed a preliminary scatter/gather browsing graphical user interface (GUI) and developed a functional prototype. We relied on Shneiderman's visual information seeking mantra [25]—overview first, zoom and filter, then details on demand—for the design process to provide overviews of clusters and to show details according to users' interest.

Figure 4:
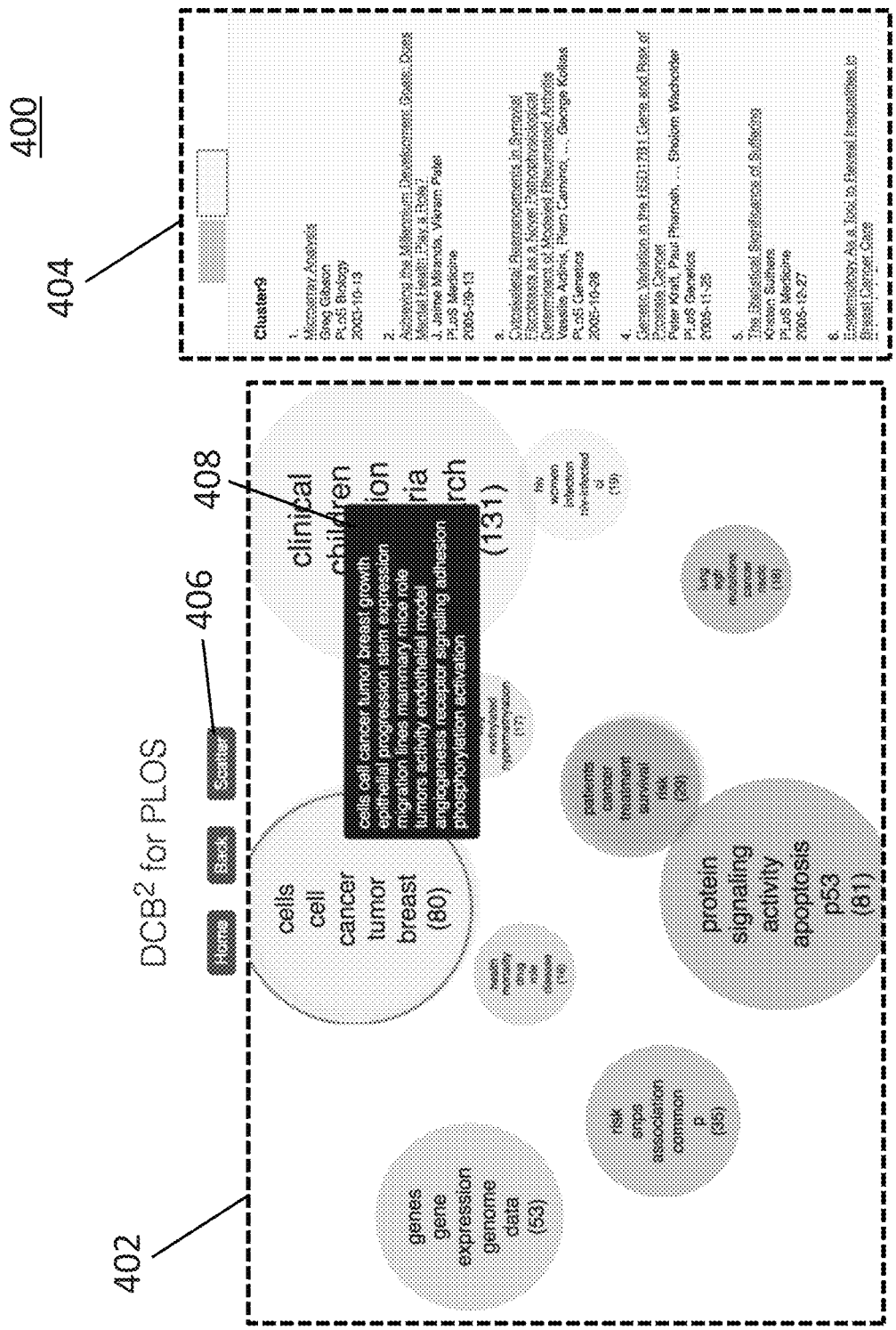
FIG. 4 is a diagram illustrating initial search results for a query "breast neoplasms" presented as topical clusters.

FIG. 4 is a diagram illustrating initial search results for a query "breast neoplasms" presented as topical clusters via an example GUI 400. In some embodiments, GUI 400 may be provided by a cluster-based search and retrieval system utilizing dynamic clustering and scatter/gather operations. As depicted, GUI 400 may include two visualization panels 402-404 and a scatter button 406 for triggering scatter operations.

Referring to GUI 400, the left panel (hereinafter cluster panel) 402 displays visual representation of clusters processed on the server-side and the right panel (hereinafter document panel) 404 presents information about documents (e.g., hyperlinks, titles, data, or related information) that are in the selected clusters in cluster panel 402.

In some embodiments, cluster centroids may correspond to coordinates in semantic space constructed by t-SNE. In such embodiments, the coordinates of two clusters' centroids may reflect their relative semantic relatedness.

In some embodiments, related terms or keywords associated with each cluster may be displayed as well as the number of documents in the respective cluster. For example, a set of representative keywords associated with a cluster may be displayed as text in its visual representation (e.g., within a circle representing a cluster) and a larger set of related terms may be displayed in a pop-up panel 408, e.g., when the mouse pointer hovers over the visual representation of the cluster. In another example, a number of documents in each cluster may be displayed as text in its visual representation (e.g., a number in parentheses within a circle representing a cluster).

In some embodiments, an area of a displayed cluster (circle) may be proportional to the number of documents associated with the cluster. In some embodiments, if users move their mouse pointer over a cluster in GUI 400, corresponding bibliographies of documents (article titles, author names, journal titles, and publication dates) with hyperlinks registered in PubMed may appear (e.g., while the mouse pointer is still hovering within the cluster) in document panel 404.

In some embodiments, a user can click one or more cluster(s) of interest for triggering a Gather process and associated references will be displayed in the document panel until the cluster(s) are deselected. Another click can deselect the cluster(s). If multiple clusters are selected, users can navigate the corresponding documents for each cluster through the tabs located at the top of the document panel. The circle in the cluster panel and its corresponding tab in the document panel are presented in the same color to facilitate intuitive navigation. Users can zoom or pan the visualization panel as needed. By clicking the "Scatter" button, the chosen clusters of documents are re-clustered (see Section 3.4) and scattered again. After examining the results, users can either try a new Scatter or return to the previous step. Users can iterate through this scatter/gather process interactively until they satisfy their information need.

3.4 Re-Clustering

Upon receiving a set of selected clusters for the gather phase, the system retrieves the document ID data within the clusters from the session data and performs a scatter phase that involves a series of processes from keyword discovery to clustering as described in Section 3.2. One may think that these processes are redundant. However, it should be stressed that these processes are crucial for the dynamicity of $DCB^2$ to identify new keywords, which would be different from the previously identified keywords and, consequently, should yield more relevant topical clusters. The descriptions of the resulting clusters and their 2D coordinates are computed in the same way as previously described and sent to the client. When the total number of articles in the selected clusters becomes smaller than a predefined threshold, their bibliographic data are also sent to the client as well for examination.

4. Evaluation

In this section, we first evaluate our sampling-based clustering approach quantitatively and then walk through the prototype system with a possible use case to demonstrate how $DCB^2$ could be used for information seeking.

4.1 Dynamic Clustering

To realize a cluster-based document browsing system for a large biomedical bibliography database, clustering should ideally be done in constant time (e.g., O(1) time) irrespective of the size of the search result. However, existing clustering algorithms running in constant time typically rely on a pre-computed static hierarchy of categories, which is not suited for iterative, dynamic cluster-based browsing.

To overcome the problem, $DCB^2$ uses a sampling-based clustering approach, retrieving only the N latest articles for a given query. Although the time complexity of the clustering algorithm itself (k-means) is not constant, the clustering process completes approximately in constant time for fixed N. The running time could be short enough to perform on the fly if N is small. On the other hand, small N would not produce clusters representative of the entire search results. Therefore, we empirically examined the relationship between the sample size (number of documents) and the quality of clusters so as to find an appropriate N which could produce clusters with the quality close to those created from the entire search results.

4.1.1 Experimental Setups. For this experiment, we needed a data set in which each document is labeled with a category or class as ground truth. Following the methodology by Ortiz et al. [16], we considered Medical Subject Headings (MeSH) major topics as categories. Specifically, we used the MeSH term "neoplasms by site" to construct our data set as follows:

(1) On the PubMed website, we used a query "Neoplasms by Site" [MeSH Major Topic] to retrieve articles on Feb. 26, 2019. We restricted the search only to PLOS journals by specifying journal names so that the resulting data set would better reflect the characteristics of the PLOS archive. Note that all the articles annotated with the MeSH terms below "Neoplasms by Site" in the MeSH hierarchy were also retrieved by this query.

(2) All the MeSH terms given to the articles were generalized to the MeSH terms right below "Neoplasms by Site". Then, six most frequent MeSH terms, "Digestive System Neoplasms" (4,416), "Breast Neoplasms" (2,647), "Urogenital Neoplasms" (2,313), "Thoracic Neoplasms" (1,770), "Endocrine Gland Neoplasms" (1,516), "Head and Neck Neoplasms" (1,413), were identified and treated as topical categories (the numbers in the parentheses show the number of articles annotated with respective MeSH terms). These six categories were chosen such that each category would have at least 1,000 articles. After deleting articles annotated with none of these MeSH terms, 12,530 articles remained.

(3) The same query as above was used to retrieve full-text articles from the PubMed Central database. From the retrieved articles, the body texts of the remaining 12,530 articles were extracted.

There are many criteria for evaluating the quality of clusters. Among them, we used Adjusted Mutual Information (AMI) following a recommendation by Romano et al. [19]. AMI is based on mutual information and is a measure of agreement between true labels and those by a clustering algorithm. It quantifies the amount of information shared between the two assignments and it is defined by term probability distributions and the information-theoretic measure of entropy. AMI is adjusted for chance by using the expected value of mutual information for normalization.

Figure 5:
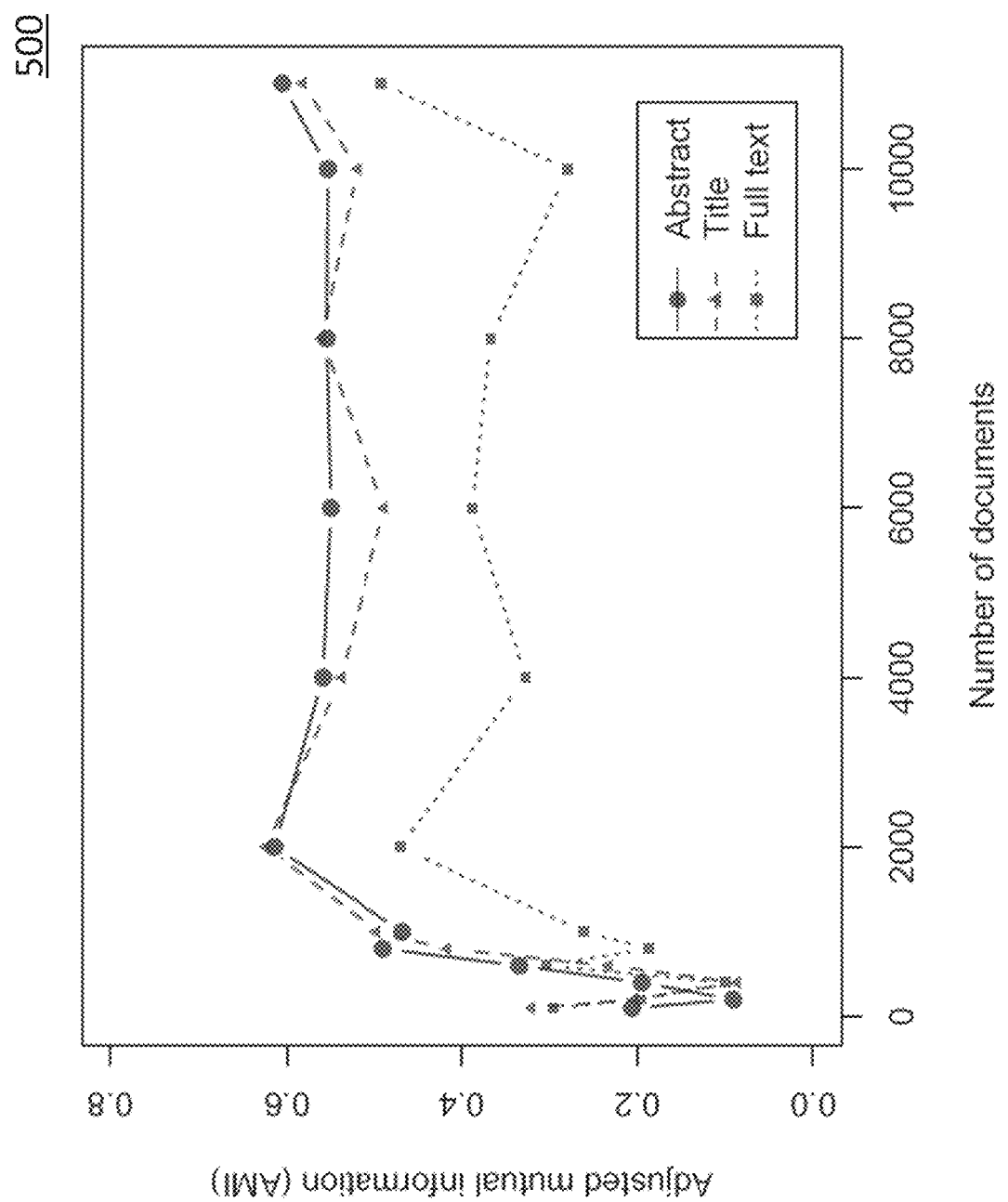
FIG. 5 is a diagram illustrating the relationship between the number of documents and cluster quality.

4.1.2 Results. FIG. 5 is a diagram 500 illustrating the relationship between the number of documents and the quality of generated clusters in AMI, where the sample size was gradually increased from 100 to 12,530. We compared three different types of data, i.e., titles only (denoted as "Title"), titles and abstracts (denoted as "Abstract"), and titles and abstracts and body texts (denoted as "Full Text"). One can observe that AMI shapely improved as the sample size increased up to 2,000 for Title and Abstract and then it became more or less stable for the rest. Somewhat unexpectedly, Titles worked comparably with Abstracts, although using abstracts tended to produce more reliable results. On the other hand, using full-text data was not as effective as using titles and/or abstracts, which is consistent with the experiment on a breast cancer subset of PubMed Central data (BRCA-FULL) [16].

Figure 6:
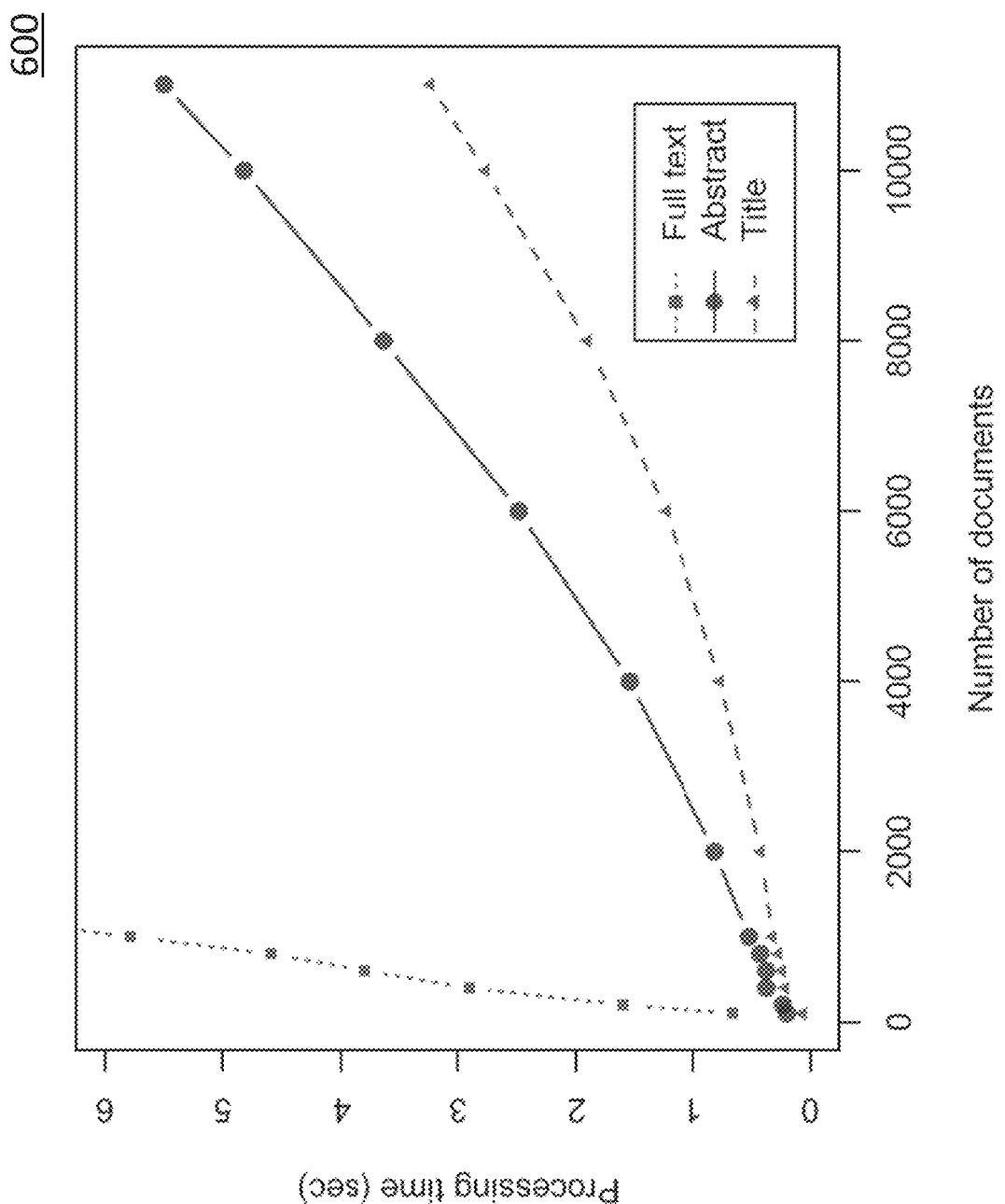
FIG. 6 is a diagram illustrating the relationship between the number of documents and processing time.

Then, we compared the processing time for clustering documents based on Title, Abstract, and Full Text. The processing time was measured from loading data to clustering. FIG. 6 is a diagram 600 illustrating the relationship between the amount or number of documents and processing time. Diagram 600 indicates that Title was the fastest, followed by Abstract, then Full Text, and the processing time grew rapidly as the number of documents increased, especially for Full Text. Based on these observations, Based on these observations, a suitable (e.g., executing in constant time or approximately constant time) technique for constructing topical clusters may involve using the 2,000 latest articles (i.e., N=2,000) and titles and abstracts (but not full text).

The validity of such parameters can be further investigated through a user study in future work.

4.2 Use Case

Figure 7:
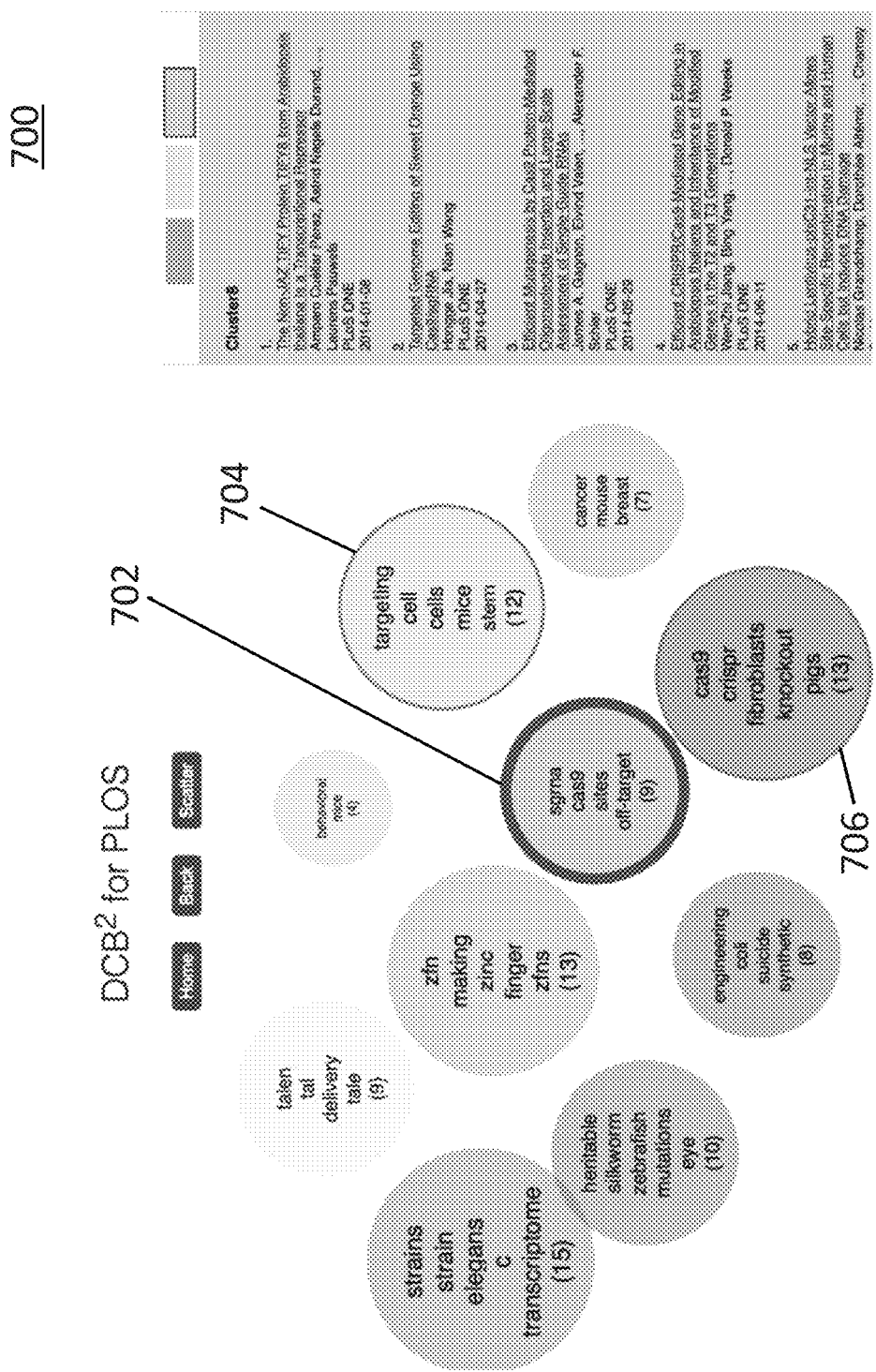
FIG. 7 is a diagram illustrating example search results for a query "genomic editing" presented as topical clusters.

FIG. 7 is a diagram 700 illustrating example search results for a query "genomic editing" presented as topical clusters. Diagram 700 indicates how a researcher would navigate through the literature using $DCB^2$. In particular, diagram 700 depicts the resulting clusters for the query "genomic editing". Referring to diagram 700, a user may select three semantically related clusters 702-706 based on a close spatial distance and an interest in the concepts of "sgrna" (single guide RNA), "sites", "off-target", "targeting", and "crispr" (clustered regularly interspaced short palindromic repeats).

In this instance, for example, assume a researcher is wanting to understand the landscape of genomic editing technologies by exploring the highly-weighted concepts and their latent associations based on spatially encoded information and then mapping the concepts back to their original publications for review when desired.

Figure 8:
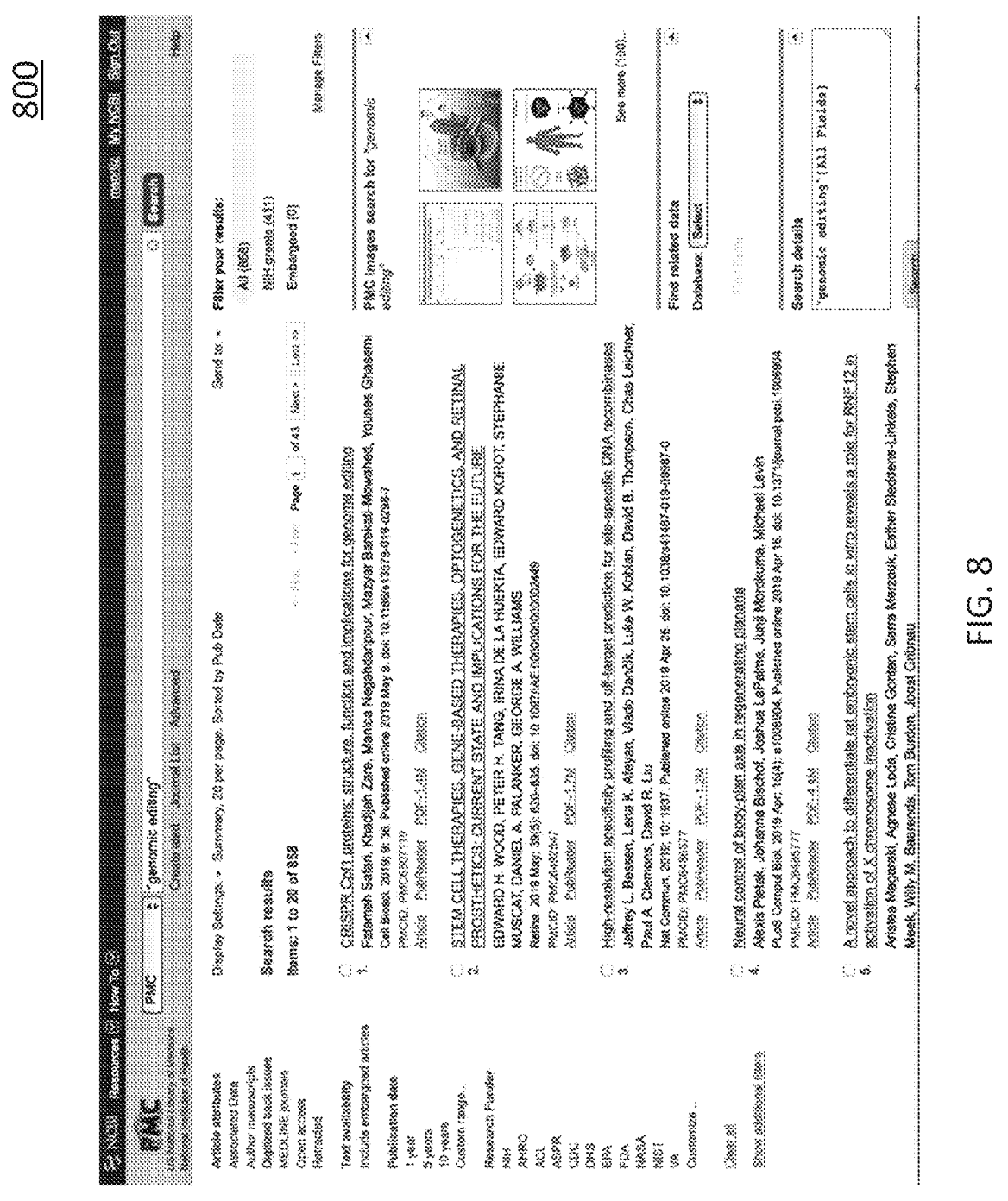

FIG. 8 is a diagram 800 illustrating search results for a query "genomic editing" using the PubMed Central website. Diagram 800 displays the results of the query from the PubMed Central website. Notably, the results include an overload of information in which the user must process and extrapolate concepts on their own, e.g., by applying filtering tools, re-formulating the query, or sequentially scrolling through the ranked results. In contrast, we believe that the scatter/gather paradigm may offer the benefit of treating searching as learning [7] in a cognitively less demanding modality.

Figure 9:
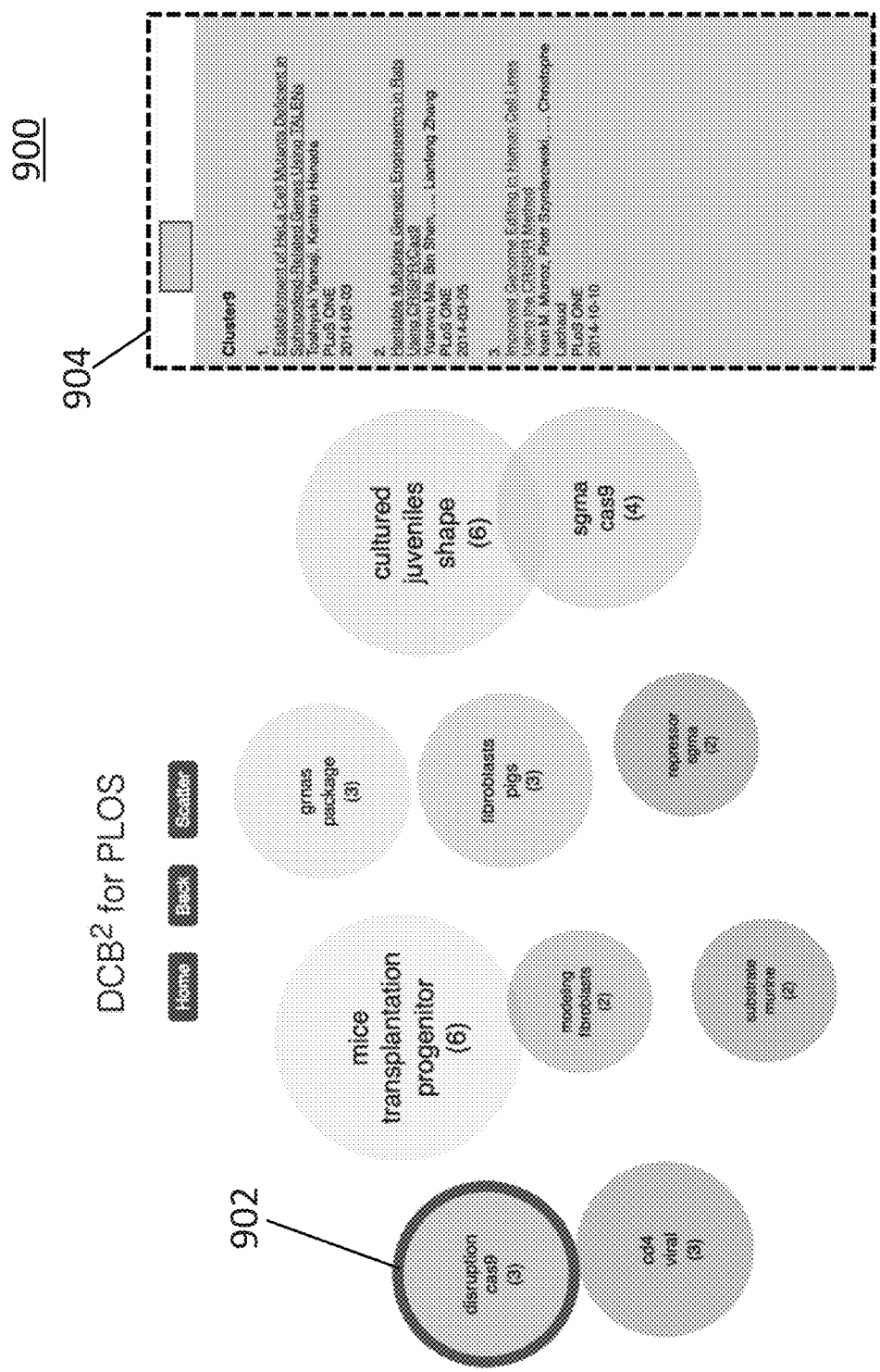
FIG. 9 is a diagram illustrating example new search results as topical clusters after a cluster related to "comparative genomics" is selected and scattered.

FIG. 9 is a diagram 900 illustrating example new search results as topical clusters after a cluster related to "comparative genomics" is selected and scattered. That is, diagram 900 shows new clusters after a Scatter phase involving a cluster related to "comparative genomics". Referring to diagram 900, in one example, a user may select a cluster 902 (e.g., "Cluster9") based on the keywords "disruption" and "cas9" (CRISPR associated protein 9) that results in a very small and specific document set on a document panel 904. In this example, a researcher can quickly learn from the document set that genome editing technologies can induce downstream effects based on an error-prone repairing mechanism that leads to mutation and gene disruption and that methods are being developed to improve the fidelity of the technology. For example, much work on improving the technology is already underway [2, 9, 14, 18, 27]

4. Discussion and Future Work

The subject matter described herein relates to various aspects for dynamic cluster-based search and retrieval including testing a prototype cluster-based document browsing system referred to herein as $DCB^2$ for exploring biomedical literature. Our prototype system adopts the scatter/gather paradigm and can provide real-time dynamic clustering, efficient and accurate representation, and/or effective presentation. To facilitate real-time dynamic clustering and efficient and accurate representation, we applied on-the-fly keyword discovery and utilized sampling-based clustering. To facilitate effective presentation, we designed and built an intuitive user interface. To demonstrate the validity of the approach, we examined the relationship between cluster quality and sample size and showed that using around 2,000 documents produced clusters that were as good as clusters generated using the entire document collection and with much less processing time. Also, a possible use case was provided to illustrate the utility of the system. Future work will examine scalability, building more efficient indices to allow faster iteration, generating interpretable descriptions for clusters, and system evaluation involving prospective users.

Figure 10:
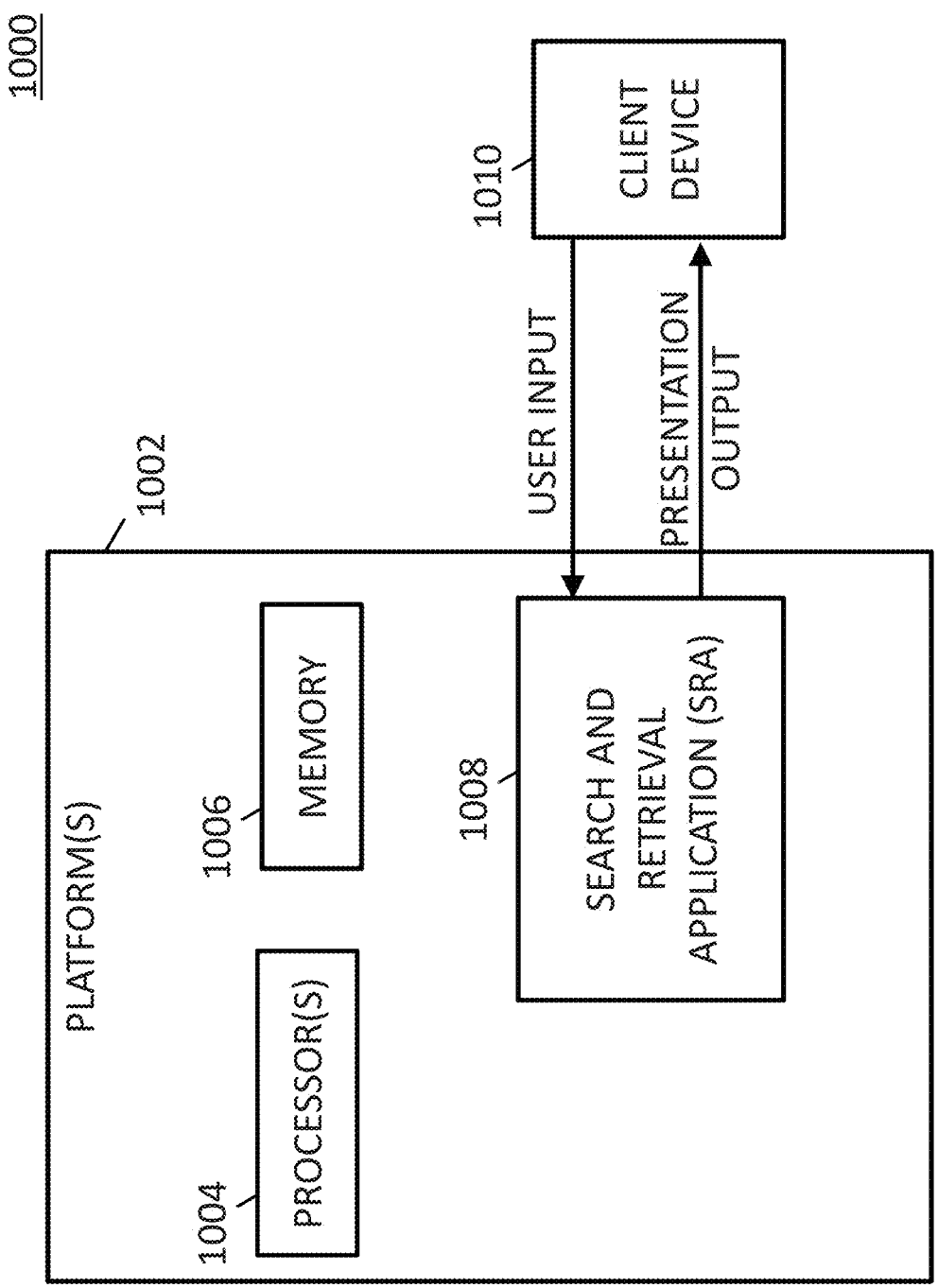
FIG. 10 is a block diagram of a system for dynamic cluster-based search and retrieval.

FIG. 10 is a block diagram of an example system 1000 for performing dynamic cluster-based search and retrieval. In FIG. 10, system 1000 may include one or more computing platform(s) 1002 (e.g., a computer server or a cloud-based or distributed system) having one or more processor(s) 1004 and memory 1006. A search and retrieval application (SRA) 1008 may reside on computing platform(s) 1002 and be executable by processor(s) 1004. SRA 1008 may receive user input (e.g., text entered on start page 300 or user selections via GUI 400) and may generate presentation information for displaying search results as visual constructs on a client device 1010 (e.g., a smartphone or computer executing a web browser). For example, SRA 1008 may send a webpage or related information for presenting search results to a user via client device 1010. In this example, using the webpage or related information, client device 1010 or related application may display search results as geometric shapes (e.g., circles, ovals, polygons, etc.) labeled with different keywords, where each shape represents a cluster of one or more related documents and where the keywords labeling the shape represent terms or phrases associated with the related documents of that cluster.

In some embodiments, SRA 1008 may utilize a scatter/gather paradigm for information search and retrieval. For example, a user may provide initial input (e.g., a text query), and, in response, SRA 1008 may perform a scatter operation involving dynamic clustering (e.g., sorting or grouping relevant documents associated with user input into various clusters) and presenting the results of the clustering to the user, e.g., by displaying circles labeled with keywords that represent the clusters of relevant documents. In this example, selecting one of the clusters by the user (e.g., clicking on a 'breast cancer' circle) may trigger a gathering operation involving determining relevant documents to use for a subsequent scatter operation. Continuing with this example, scatter and gather operations may continue until the user identifies one or more appropriate results (e.g., a relevant document or a group of relevant documents on a particular topic) or until a stopping event occurs, e.g., when a threshold value is reached or exceeded.

In some embodiments, threshold values may be static or predetermined values. For example, an example threshold value may involve a certain number of documents to be analyzed, searched, or grouped. In another example, an example threshold value may involve a maximum processing time based on predetermined settings.

In some embodiments, threshold values may be dynamic or variable. For example, an example threshold value may be reached when the number of relevant documents associated with user input or a search is less than or equal to the number of clusters generated by the search. In another example, an example threshold value may involve a maximum processing time based on dynamic conditions, e.g., current server processing workload.

In some embodiments, computing platform(s) 1002 with SRA 1008 may be remotely located respective to a user or client device 1010, e.g., part of different networks or in different cities, states, or countries. In such embodiments, client device 1010 may be a smartphone running a web browser or a standalone application that interacts with SRA 1008 or a related web server via the internet. For example, SRA 1008 may receive user input from client device 1010, may perform search and retrieval operations (e.g., gather and scatter operations), and may provide, as output, presentation information (e.g., a web page, data packets, and/or keywords and coordinates information for displaying clusters) to client device 1010, e.g., via a web browser.

In some embodiments, computing platform(s) 102 with SRA 1008 may be local to a user or client device 1010, e.g., in a same room or network. In such embodiments, client device 1010 may be a computer or virtual machine running a search and retrieval application that interacts with SRA 1008 or a related server. For example, SRA 1008 may receive user input from client device 1010, may perform search and retrieval operations (e.g., gather and scatter operations), and may provide, as output, presentation information (e.g., a web page, data packets, and/or keywords and coordinates information for displaying clusters) to client device 1010, e.g., via a web browser. In some embodiments, client device 1010 or related functionality (e.g., GUI 400) may be implemented on or using computing platform(s) 102. For example, a 'front-end' application for providing users a GUI for interacting with SRA 1008 may be implemented on the same computer or device executing SRA 1008.

It will be appreciated that FIG. 10 is for illustrative purposes and that various entities, their locations, and/or their functions may be changed, altered, added, or removed. For example, some entities and/or functions may be combined into a single entity. In another example, an entity and/or function may be located at or implemented by two or more entities.

Figure 11:
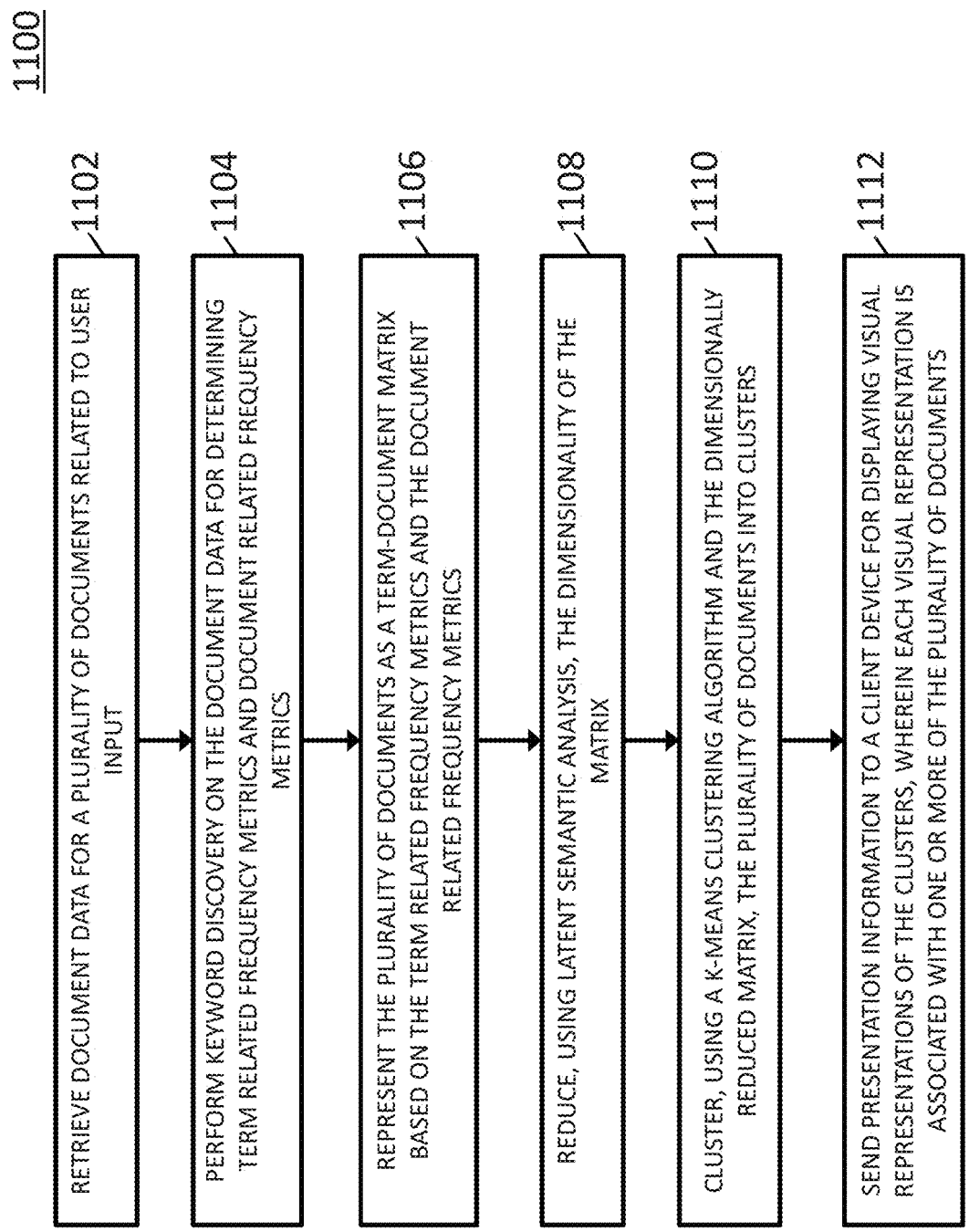
FIG. 11 is a flow chart illustrating an exemplary process for dynamic cluster-based search and retrieval.

FIG. 11 is a flow chart illustrating an example process 1100 for using SRA 1008 for dynamic cluster-based search and retrieval. In some embodiments, process 1100 described herein, or portions thereof, may be performed at or by system 1000, computing platform(s) 1002, SRA 1008, and/or another module or device. For example, computing platform(s) 1002 may include a server, a computer, or other equipment and SRA 1008 may include various data algorithms executing on computing platform(s) 1002 for identifying relevant documents associated with user input, for dynamically clustering related documents into clusters, and for providing presentation information for displaying the clusters or related information. In some embodiments, process 1100 may include steps 1102-1112.

In step 1102, document data for a plurality of documents related to user input may be retrieved. In some embodiments, document data (e.g., used by SRA 1008) may include document titles, document abstracts, document body text, document identifiers, source identifiers, authors, and/or document dates.

In some embodiments, retrieving document data for a plurality of documents related to user input may include using the user input or a predefined related term to query a data store containing document data for multiple documents, wherein each of the plurality of documents related to the user input has document data that matches the user input or the predefined related term.

In step 1104, keyword discovery may be performed on the document data for determining term related frequency metrics and document related frequency metrics.

In step 1106, the plurality of documents may be represented as a term-document matrix based on the term related frequency metrics and the document related frequency metrics.

In step 1108, the dimensionality of the matrix may be reduced using latent semantic analysis. In some embodiments, reducing, using latent semantic analysis, the dimensionality of a term-document matrix may include decomposing, using singular value decomposition, the matrix into two orthogonal matrices and a diagonal matrix.

In step 1110, the plurality of documents may be clustered into clusters using a k-means clustering algorithm and the dimensionally reduced matrix.

In step 1112, presentation information may be sent to client device 1010 for displaying visual representations of the clusters, wherein each visual representation is associated with one or more of the plurality of documents.

In some embodiments, the size of each visual representation of a cluster is based on the amount of documents in the cluster. For example, in a GUI for displaying search results associated with SRA 1008, the area of a first circle representing a cluster of 30 documents may be less than a second circle representing a second cluster of 500 documents but greater than a third circle representing a third cluster of 15 documents.

In some embodiments, sending presentation information may include sending related keywords for the clusters and spatial information (e.g., 2D coordinates) for the clusters.

In some embodiments, related keywords for a cluster may be determined by identifying a centroid of the cluster (e.g., as based on the coordinates of the cluster in two-dimensional space); transforming the centroid to a term vector containing term frequency information; and determining the related keywords based on terms with the highest frequency as indicated by the term vector.

In some embodiments, spatial information for a cluster may be determined by transforming a centroid of the cluster to coordinate space using t-SNE.

In some embodiments, SRA 1008 and/or another entity may receive an indication of a user selecting a first visual representation of a first cluster, identify documents associated with the first cluster, perform dynamic clustering of the documents associated with the first cluster into new clusters, and send additional presentation information to client device 1010 for displaying visual representations of the new clusters.

It will be appreciated that process 1100 is for illustrative purposes and that different and/or additional actions may be used. It will also be appreciated that various actions described herein may occur in a different order or sequence.

It should be noted that system 1000, computing platform(s) 1002, SRA 1008, and/or functionality described herein may constitute a special purpose computing device. Further, system 1000, computing platform(s) 1002, SRA 1008, and/or functionality described herein can improve the technological field for data search and discovery. For example, by using dynamic clustering, related search results can be presented to a user in a visually informative way and can aid the user in their information exploration, especially for dense information spaces. Further, by using a scatter/gather model, a user can identify related topics and search terms without having prior understanding of terminology or information space structure.

The disclosure of each of the following references is incorporated herein by reference in its entirety.

REFERENCES

[1] David Arthur and Sergei Vassilvitskii. 2007. k-means++: The advantages of careful seeding. In Proceedings of the eighteenth annual ACM-SIAM symposium on Discrete algorithms. Society for Industrial and Applied Mathematics, 1027-1035.

[2] Nurit Assia Batzir, Adi Tovin, and Ayal Hendel. 2017. Therapeutic Genome Editing and its Potential Enhancement through CRISPR Guide RNA and Cas9 Modifications. Pediatric endocrinology reviews: PER 14, 4 (2017), 353-363.

[3] Douglass R. Cutting, David R. Karger, and Jan O. Pedersen. 1993. Constant Interaction-time Scatter/Gather Browsing of Very Large Document Collections. In Proceedings of the 16th Annual International ACM SIGIR Conference on Research and Development in Information Retrieval (SIGIR '93). ACM, New York, NY, USA, 126-134. https://doi.org/10.1145/160688.160706

[4] Douglass R. Cutting, David R. Karger, Jan O. Pedersen, and John W. Tukey. 1992. Scatter/Gather: A Cluster-based Approach to Browsing Large Document Collections. In Proceedings of the 15th Annual International ACM SIGIR Conference on Research and Development in Information Retrieval (SIGIR '92). ACM, New York, NY, USA, 318-329. https://doi.org/10.1145/133160.133214

[5] Souvick Ghosh, Manasa Rath, and Chirag Shah. 2018. Searching as Learning: Exploring Search Behavior and Learning Outcomes in Learning-related Tasks. In Proceedings of the 2018 Conference on Human Information Interaction & Retrieval. ACM, 22-31.

[6] Xuemei Gong, Weimao Ke, Yan Zhang, and Ramona Broussard. 2013. Interactive Search Result Clustering: A Study of User Behavior and Retrieval Effectiveness. In Proceedings of the 13th ACM/IEEE-CS Joint Conference on Digital Libraries (JCDL '13). ACM, New York, NY, USA, 167-170. https://doi.org/10.1145/2467696.2467726

[7] Preben Hansen and Soo Young Rieh. 2016. Recent advances on searching as learning: An introduction to the special issue.

[8] Marti A. Hearst and Jan O. Pedersen. 1996. Reexamining the Cluster Hypothesis: Scatter/Gather on Retrieval Results. In Proceedings of the 19th Annual International ACM SIGIR Conference on Research and Development in Information Retrieval (SIGIR '96). ACM, New York, NY, USA, 76-84. https://doi.org/10.1145/243199.243216

[9] Melissa L Kelley, aklina Strezoska, Kaizhang He, Annaleen Vermeulen, and Anja van Brabant Smith. 2016. Versatility of chemically synthesized guide RNAs for CRISPR-Cas9 genome editing. Journal of biotechnology 233 (2016), 74-83.

[10] Bill Kules, Robert Capra, Matthew Banta, and Tito Sierra. 2009. What do exploratory searchers look at in a faceted search interface?. In Proceedings of the 9th ACM/IEEE-CS joint conference on Digital libraries. ACM, 313-322.

[11] Thomas K Landauer, Peter W Foltz, and Darrell Laham. 1998. An introduction to latent semantic analysis. Discourse processes 25, 2-3 (1998), 259-284.

[12] Gary Marchionini. 2006. Exploratory search: from finding to understanding. Commun. ACM 49, 4 (2006), 41-46.

[13] Gary Marchionini. 2006. Exploratory Search: From Finding to Understanding. Commun. ACM 49, 4 (April 2006), 41-46. https://doi.org/10.1145/1121949.1121979

[14] Su Bin Moon, Jeong-Heon Ko, Jin-Soo Kim, Yong-Sam Kim, et al. 2019. Improving CRISPR Genome Editing by Engineering Guide RNAs. Trends in biotechnology (2019).

[15] J. Mostafa, L. M. Quiroga, and M. Palakal. 1998. Filtering medical documents using automated and human classification methods. Journal of the American Society for Information Science 49, 14 (1998), 1304-1318.

[16] Michael Segundo Ortiz, Kazuhiro Seki, and Javed Mostafa. 2018. Toward Exploratory Search in Biomedicine: Evaluating Document Clusters by MeSH as a Semantic Anchor. CoRR arXiv:1812.02129 (2018). arXiv:1812.02129 https://arxiv.org/abs/1812.02129

[17] C. J. Van Rijsbergen. 1979. Information Retrieval (2nd ed.). Butterworth-Heinemann, Newton, MA, USA.

[18] Khadim Hussain Rimsha Farooq, Shahid Nazir, Muhammad Rizwan Javed, and Nazish Masood. 2018. CRISPR/Cas9; A robust technology for producing genetically engineered plants. Cell Mol Biol (Noisy le Grand) 64, 14 (2018).

[19] Simone Romano, Nguyen Xuan Vinh, James Bailey, and Karin Verspoor. 2016. Adjusting for chance clustering comparison measures. The Journal of Machine Learning Research 17, 1 (2016), 4635-4666.

[20] Tuukka Ruotsalo, Giulio Jacucci, Petri Myllymäki, and Samuel Kaski. 2014. Interactive Intent Modeling: Information Discovery Beyond Search. Commun. ACM 58, 1 (December 2014), 86-92. https://doi.org/10.1145/2656334
[21] Tuukka Ruotsalo, Jaakko Peltonen, Manuel J. A. Eugster, Dorota Glowacka, Patrik Floréen, Petri Myllymäki, Giulio Jacucci, and Samuel Kaski. 2018. Interactive Intent Modeling for Exploratory Search. ACM Trans. Inf. Syst. 36, 4, Article 44 (October 2018), 46 pages. https://doi.org/10.1145/3231593
[22] Cecilia Di Sciascio, Vedran Sabol, and Eduardo Veas. 2017. Supporting Exploratory Search with a Visual User-Driven Approach. ACM Trans. Interact. Intell. Syst. 7, 4, Article 18 (December 2017), 35 pages. https://doi.org/10.1145/3009976
[23] D Sculley. 2010. Web-scale k-means Clustering. In Proceedings of the 19th International Conference on World Wide Web (WWW '10). ACM, New York, NY, USA, 1177-1178. https://doi.org/10.1145/1772690.1772862
[24] Hui Shi, Wu He, and Guandong Xu. 2018. Workshop Proposal on Knowledge Discovery from Digital Libraries. In Proceedings of the ACM/IEEE Joint Conference on Digital Libraries.
[25] Ben Shneiderman. 1996. The Eyes Have It: A Task by Data Type Taxonomy for Information Visualizations. In Proceedings of the 1996 IEEE Symposium on Visual Languages (VL '96). IEEE Computer Society, Washington, DC, USA, 336-343. http://dl.acm.org/citation.cfm?id=832277.834354
[26] Karen Sparck Jones. 1972. Statistical interpretation of term specificity and its application in retrieval. Journal of Documentation 28, 1 (1972), 11-20.
[27] Fei Teng, Tongtong Cui, Qingqin Gao, Lu Guo, Qi Zhou, and Wei Li. 2019. Artificial sgRNAs engineered for genome editing with new Cas12b orthologs. Cell discovery 5, 1 (2019), 23.
[28] Laurens van der Maaten and Geoffrey Hinton. 2008. Visualizing Data using t-SNE. Journal of Machine Learning Research 9 (2008), 2579-2605.
[29] Ryen W White, Bill Kules, Steven M Drucker, et al. 2006. Supporting exploratory search, introduction, special issue, communications of the ACM. Commun. ACM 49, 4 (2006), 36-39.
[30] Ryen W White and Resa A Roth. 2009. Exploratory search: Beyond the query-response paradigm. Synthesis lectures on information concepts, retrieval, and services 1, 1 (2009), 1-98.
[31] Max Wilson, Alistair Russell, Daniel A Smith, et al. 2006. mSpace: improving information access to multimedia domains with multimodal exploratory search. Commun. ACM 49, 4 (2006), 47-49.

Although specific examples and features have been described above, these examples and features are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed in this specification (either explicitly or implicitly), or any generalization of features disclosed, whether or not such features or generalizations mitigate any or all of the problems described in this specification. Accordingly, new claims may be formulated during prosecution of this application (or an application claiming priority to this application) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A method for dynamic cluster-based search and retrieval, the method comprising:
    al a server:
        retrieving document data for a plurality of documents related to user input:
        performing keyword discovery on the document data for determining term related frequency metrics and document related frequency metrics:
        representing the plurality of documents as a term-document matrix based on the term related frequency metrics and the document related frequency metrics:
        reducing, using latent semantic analysis, the dimensionality of the matrix:
        clustering, using a sampling-based k-means clustering algorithm and the dimensionally reduced matrix, the plurality of documents into clusters, wherein the plurality of documents is a predetermined number of most recent documents related to the user input, wherein the most recent documents are determined using document dates in a data store, wherein the sampling-based k-means clustering algorithm executes in constant or near constant time: and
        sending presentation information to a client device for displaying visual representations of the clusters, wherein each of the visual representations is associated with one or more of the plurality of documents, wherein sending the presentation information includes sending related keywords for the clusters and spatial information for the clusters, and wherein the related keywords for the clusters are determined by:
    for each of the clusters:
        identifying a centroid of the cluster:
        transforming the centroid to a term vector containing term frequency information; and
        determining the related keywords based on terms with the highest frequency as indicated by the term vector.

2. The method of claim 1 wherein the document data includes document titles, document abstracts, document body text, document identifiers, source identifiers, authors, or the document dates.

3. The method of claim 1 wherein retrieving the document data for the plurality of documents related to the user input includes using the user input or a predefined related term to query the data store containing the document data for the plurality of documents, wherein each of the plurality of documents related to the user input has document data that matches the user input or the predefined related term.

4. The method of claim 1 where reducing, using latent semantic analysis, the dimensionality of the matrix includes decomposing, using singular value decomposition, the matrix into two orthogonal matrices and a diagonal matrix.

5. The method of claim 1 wherein the size of each visual representation of a cluster is based on the number of documents in the cluster.

6. The method of claim 1 wherein the spatial information for the clusters is determined by transforming the centroid of each cluster to coordinate space using t-Distributed Stochastic Neighbor Embedding (t-SNE).

7. The method of claim 1 comprising:
receiving an indication of a user selecting a first visual representation of a first cluster,
identifying documents associated with the first cluster,
performing dynamic clustering of the documents associated with the first cluster into new clusters, and
sending additional presentation information to the client device for displasia visual representations of the new clusters.

8. A system for dynamic cluster-based search and retrieval, the system comprising:
a computing platform including at least one processor:
a search and retrieval application executable by the at least one processor for:
retrieving document data for a plurality of documents related to user input:
performing keyword discovery on the document data for determining term related frequency metrics and document related frequency metrics:
representing the plurality of documents as a term-document matrix based on the term related frequency metrics and the document related frequency metrics:
reducing, using latent semantic analysis, the dimensionality of the matrix:
clustering, using a sampling-based k-means clustering algorithm and the dimensionally reduced matrix, the plurality of documents into clusters, wherein the plurality of documents is a predetermined number of most recent documents related to the user input, wherein the most recent documents are determined using document dates in a data store, wherein the sampling-based k-means clustering algorithm executes in constant or near constant time; and
sending presentation information to a client device for displaying visual representations of the clusters, wherein each of the visual representations is associated with one or more of the plurality of documents, wherein sending the presentation information includes sending related keywords for the clusters and spatial information for the clusters, and wherein the related keywords for the clusters are determined by:
for each of the clusters:
identifying a centroid of the cluster;
transforming the centroid to a term vector containing term frequency information; and
determining the related keywords based on terms with the highest frequency as indicated by the term vector.

9. The system of claim 8 wherein the document data includes document titles, document abstracts, document body text, document identifiers, source identifiers, authors, or the document gates.

10. The system of claim 8 wherein retrieving the document data for the plurality of documents related to the user input includes using the user input or a predefined related term to query the data store containing the document data for the plurality of documents, wherein each of the plurality of documents related to the user input has document data that matches the user input or the predefined related term.

11. The system of claim 8 where reducing, using latent semantic analysis, the dimensionality of the matrix includes decomposing, using singular value decomposition, the matrix into two orthogonal matrices and a diagonal matrix.

12. The system of claim 8 wherein the size of each visual representation of a cluster is based on the number of documents in the cluster.

13. The system of claim 8 wherein the spatial information for the clusters is determined by transforming the centroid of each cluster to coordinate space using t-Distributed Stochastic Neighbor Embedding (t-SNE).

14. The system of claim 8 wherein the search and retrieval application is configured for:
receiving an indication of a user selecting a first visual representation of a first cluster,
identifying documents associated with the first cluster,
performing dynamic clustering of the documents associated with the first cluster into new clusters, and
sending additional presentation information to the client device for displaying visual representations of the new clusters.

15. A non-transitory computer readable medium having stored thereon executable instructions that when executed by at least one processor of a computer cause the computer to perform steps comprising: al a server retrieving document data for a plurality of documents related to user input:
performing keyword discovery on the document data for determining term related frequency metrics and document related frequency metrics:
representing the plurality of documents as a term-document matrix based on the term related frequency metrics and the document related frequency metrics:
reducing, using latent semantic analysis, the dimensionality of the matrix:
clustering, using a sampling-based k-means clustering algorithm and the dimensionally reduced matrix, the plurality of documents into clusters, wherein the plurality of documents is a predetermined number of most recent documents related to the user input, wherein the most recent documents are determined using document dates in a data store, wherein the sampling-based k-means clustering algorithm executes in constant or near constant time; and
sending presentation information to a client device for displaying visual representations of the clusters, wherein each of the visual representations is associated with one or more of the plurality of documents, wherein sending the presentation information includes sending related keywords for the clusters and spatial information for the clusters, and wherein the related keywords for the clusters are determined by:
for each of the clusters:
identifying a centroid of the cluster;
transforming the centroid to a term vector containing term frequency information; and
determining the related keywords based on terms with the highest frequency as indicated by the term vector.

16. The non-transitory computer readable medium of claim 15 wherein the document data includes document titles, document abstracts, document body text, document identifiers, source identifiers, authors, or the document dates.

* * * * *